US011278740B2

(12) United States Patent
Traboulsi et al.

(10) Patent No.: US 11,278,740 B2
(45) Date of Patent: Mar. 22, 2022

(54) TEMPORARY TATTOO COVER AND RELATED METHOD

(75) Inventors: Maeghan E. Traboulsi, Boston, MA (US); Mark Broyles, Plainville, CT (US)

(73) Assignee: BERKLEY CORPORATION, Bristol, CT (US)

( * ) Notice: Subject to any disclaimer, the term of this patent is extended or adjusted under 35 U.S.C. 154(b) by 717 days.

(21) Appl. No.: 12/264,204

(22) Filed: Nov. 3, 2008

(65) Prior Publication Data

US 2010/0113860 A1    May 6, 2010

(51) Int. Cl.
*A61N 5/10* (2006.01)
*A61B 90/00* (2016.01)

(52) U.S. Cl.
CPC .... *A61N 5/1049* (2013.01); *A61B 2090/3937* (2016.02); *Y10T 428/1486* (2015.01)

(58) Field of Classification Search
CPC ............... A61F 13/00059; A61F 15/00; G09F 2003/0208; G09F 2003/0226; G09F 2003/0227; G09F 2003/0229; G09F 2003/0258; A61N 5/1049; A61B 2019/5437
USPC ............ 128/897; 602/41, 54, 57, 60; 40/638
See application file for complete search history.

(56) References Cited

U.S. PATENT DOCUMENTS

| 168,063 A | 9/1875 | Taylor |
|---|---|---|
| 2,304,787 A | 12/1942 | Stanton |
| 2,532,011 A | 11/1950 | Dahlquist et al. |
| 2,905,174 A | 9/1959 | Smith |
| RE24,906 E | 12/1960 | Ulrich |
| 3,169,895 A | 2/1965 | Sohn |
| 3,203,125 A | 8/1965 | Stoessel |
| 3,267,623 A | 8/1966 | Block |
| 3,389,827 A | 6/1968 | Abere et al. |
| 3,487,832 A | 1/1970 | Spence |
| 3,655,494 A | 4/1972 | Buzzell |

(Continued)

FOREIGN PATENT DOCUMENTS

EP    1225208 A1    7/2002

OTHER PUBLICATIONS

DeviantArt (https://www.deviantart.com/art/Shapeset-04-Crosshairs-36547539, dated Jul. 19, 2006, accessed online on Aug. 24, 2017).*

(Continued)

*Primary Examiner* — Kaylee R Wilson
(74) *Attorney, Agent, or Firm* — McCarter & English, LLP (57) ABSTRACT

A cover for protecting a temporary mark on a person's skin includes a transparent layer and an associated opaque layer, wherein the opaque layer features an opening through which the temporary mark may be located as the cover is applied. An adhesive is superimposed upon the transparent layer in order to releasably affix the cover to the temporary mark, and also to permit maintaining the cover on a backing material during transportation or storage. During use, the mark is sighted through the transparent layer and the opening in the opaque layer, and applied to the patient's skin. The opaque layer is then removed from the transparent layer, which remains in place over the temporary mark, permitting the person to bathe or otherwise participate unhindered in his or her life's routines without smudging, wearing or removing the mark.

25 Claims, 6 Drawing Sheets

(56) References Cited

U.S. PATENT DOCUMENTS

| | | | |
|---|---|---|---|
| 3,895,456 A | 7/1975 | Fabre | |
| 4,044,708 A | 8/1977 | Klein | |
| 4,112,213 A | 9/1978 | Waldman | |
| 4,131,226 A | 12/1978 | Breiter et al. | |
| 4,217,164 A | 8/1980 | La Mers | |
| 4,310,509 A | 1/1982 | Berglund et al. | |
| 4,323,557 A | 4/1982 | Rosso et al. | |
| 4,372,303 A | 2/1983 | Grossmann et al. | |
| 4,454,180 A | 6/1984 | La Mers | |
| 4,464,834 A | 8/1984 | Simms | |
| 4,499,896 A | 2/1985 | Heinecke | |
| 4,506,676 A * | 3/1985 | Duska | G03B 42/047 378/162 |
| 4,545,371 A | 10/1985 | Grossmann et al. | |
| 4,558,980 A | 12/1985 | Sturdivan | |
| 4,597,206 A | 7/1986 | Benson | |
| 4,646,731 A | 3/1987 | Brower | |
| 4,664,106 A | 5/1987 | Snedeker | |
| 4,737,410 A | 4/1988 | Kantner | |
| 4,741,793 A | 5/1988 | Jones | |
| 4,787,158 A | 11/1988 | Vitol | |
| 4,807,755 A | 2/1989 | Jones | |
| 4,822,017 A | 4/1989 | Griesmyer | |
| 4,884,563 A | 12/1989 | Sessions | |
| 4,987,019 A | 1/1991 | Jones | |
| 5,000,172 A * | 3/1991 | Ward | A61F 13/023 128/888 |
| 5,018,516 A | 5/1991 | Gilman | |
| D319,669 S | 9/1991 | Kronberg | |
| RE33,727 E | 10/1991 | Sims | |
| 5,061,334 A | 10/1991 | Paules | |
| 5,088,483 A | 2/1992 | Heinecke | |
| 5,106,629 A | 4/1992 | Cartmell et al. | |
| 5,127,676 A | 7/1992 | Bockairo | |
| 5,153,040 A | 10/1992 | Faasse, Jr. | |
| 5,160,315 A | 11/1992 | Heinecke et al. | |
| D331,575 S | 12/1992 | Pike | |
| 5,188,424 A | 2/1993 | Herron | |
| 5,193,106 A | 3/1993 | DeSena | |
| 5,264,218 A | 11/1993 | Rogozinski | |
| 5,266,371 A | 11/1993 | Sugii | |
| 5,306,271 A * | 4/1994 | Zinreich | A61N 5/1049 378/162 |
| 5,310,402 A * | 5/1994 | Rollband | 602/42 |
| 5,336,162 A | 9/1994 | Ota et al. | |
| 5,372,589 A | 12/1994 | Davis | |
| 5,395,675 A | 3/1995 | Altholz et al. | |
| 5,407,440 A | 4/1995 | Zinreich et al. | |
| 5,411,167 A | 5/1995 | Weder | |
| 5,450,046 A | 9/1995 | Kosugi et al. | |
| 5,470,351 A | 11/1995 | Ross et al. | |
| 5,489,252 A | 2/1996 | May | |
| 5,489,262 A | 2/1996 | Cartmell et al. | |
| 5,514,442 A | 5/1996 | Galda et al. | |
| 5,520,629 A | 5/1996 | Heinecke et al. | |
| 5,531,855 A | 7/1996 | Heinecke et al. | |
| 5,573,621 A | 11/1996 | Boreali | |
| 5,603,197 A | 2/1997 | Weder | |
| 5,657,198 A | 8/1997 | Flener | |
| 5,712,767 A | 1/1998 | Koizumi | |
| 5,722,943 A | 3/1998 | Sessions | |
| 5,738,642 A | 4/1998 | Heinecke et al. | |
| 5,743,899 A * | 4/1998 | Zinreich | A61B 5/6842 428/40.2 |
| 5,752,967 A * | 5/1998 | Kritzinger et al. | 606/166 |
| 5,755,681 A | 5/1998 | Plews | |
| 5,788,284 A | 8/1998 | Hirst | |
| 5,792,092 A | 8/1998 | Turngren | |
| 5,800,894 A | 9/1998 | Navis | |
| 5,830,550 A | 11/1998 | Treleaven et al. | |
| 5,846,623 A | 12/1998 | Denny | |
| 5,863,628 A | 1/1999 | Barry | |
| D405,116 S | 2/1999 | Anderson, II | |
| 5,887,590 A | 3/1999 | Price | |
| D408,541 S | 4/1999 | Dunshee et al. | |
| 5,891,078 A * | 4/1999 | Turngren | A61F 13/0279 206/441 |
| 5,931,800 A | 8/1999 | Rasmussen et al. | |
| 5,951,505 A | 9/1999 | Gilman et al. | |
| 6,008,429 A | 12/1999 | Ritger | |
| 6,043,406 A | 3/2000 | Sessions et al. | |
| D430,674 S | 9/2000 | Dunshee et al. | |
| 6,124,522 A | 9/2000 | Schroeder | |
| 6,149,614 A | 11/2000 | Dunshee et al. | |
| 6,169,224 B1 | 1/2001 | Heinecke et al. | |
| 6,237,913 B1 | 5/2001 | Kamille | |
| D444,010 S | 6/2001 | Ambrosio | |
| 6,269,148 B1 | 7/2001 | Jessop et al. | |
| 6,280,549 B1 | 8/2001 | Langan | |
| 6,315,480 B1 | 11/2001 | Martel et al. | |
| 6,316,073 B1 | 11/2001 | Hiscock et al. | |
| 6,350,339 B1 | 2/2002 | Sessions | |
| D454,910 S | 3/2002 | Smith et al. | |
| D454,955 S | 3/2002 | Dunshee et al. | |
| 6,379,790 B1 | 4/2002 | Langan | |
| 6,408,916 B1 | 6/2002 | Anderson et al. | |
| 6,440,513 B1 | 8/2002 | Kibele et al. | |
| 6,543,809 B1 | 4/2003 | Kistner et al. | |
| 6,622,728 B2 * | 9/2003 | Rusin | A61B 5/441 128/897 |
| 6,635,004 B2 | 10/2003 | Conger | |
| D483,959 S | 12/2003 | Howard et al. | |
| 6,656,558 B1 | 12/2003 | Sarajian | |
| 6,685,682 B1 * | 2/2004 | Heinecke et al. | 604/307 |
| 6,708,940 B2 | 3/2004 | Worthley | |
| 6,833,128 B2 * | 12/2004 | Kamimoto | A61K 49/0006 424/9.8 |
| 6,945,936 B1 | 9/2005 | Kerr | |
| D517,122 S | 3/2006 | Milliorn | |
| 7,342,850 B2 | 3/2008 | Martens et al. | |
| 7,559,669 B2 | 7/2009 | Lin | |
| D599,849 S | 9/2009 | Halbur et al. | |
| 7,625,619 B2 | 12/2009 | Hodson et al. | |
| 7,781,041 B2 * | 8/2010 | Broyles | A61F 15/00 428/40.1 |
| D624,814 S | 10/2010 | Hoppner et al. | |
| D642,936 S | 8/2011 | Hoppner et al. | |
| D653,286 S | 1/2012 | Haas | |
| 8,669,827 B2 | 3/2014 | Popelka et al. | |
| 9,750,652 B1 * | 9/2017 | Broyles | A61F 15/00 |
| 2002/0107466 A1 * | 8/2002 | Faasse, Jr. | A61F 13/0259 602/57 |
| 2002/0115954 A1 | 8/2002 | Worthley | |
| 2002/0138024 A1 * | 9/2002 | Oladipo | A61F 13/041 602/3 |
| 2003/0182815 A1 | 10/2003 | Carlson, II | |
| 2004/0116802 A1 | 6/2004 | Jessop et al. | |
| 2004/0127838 A1 | 7/2004 | Jeziak | |
| 2005/0000133 A1 * | 1/2005 | Russell | A61B 90/39 40/630 |
| 2006/0111656 A1 * | 5/2006 | Broyles | 602/42 |
| 2008/0039866 A1 * | 2/2008 | Stetz | A61B 90/11 606/129 |
| 2010/0047510 A1 * | 2/2010 | Couvillion | 428/66.5 |

OTHER PUBLICATIONS

3M Health Care, 3M Tegaderm and 3M Tegaderm HP Transparent Dressings, Application Instructions, Copyright 1999, 3M Health Care Prods, and Svcs. Division, London, Ontario, Can.

* cited by examiner

TEMPORARY TATTOO COVER AND RELATED METHOD

FIELD OF THE INVENTION

The present invention generally relates to adhesive skin coverings and methods, and more particularly, to such coverings and methods for protecting a mark on a person's skin, such as a temporary tattoo applied to a person's skin for use in radiation therapy.

BACKGROUND

Temporary marks are frequently applied to a patient's skin in preparation for extended treatment programs, such as radiation therapy. Such marks are particularly critical for ensuring that treatment, such as applied radiation, is precisely focused on the appropriate area of the patient's body, and may be made with markers, pens, or other marking means.

In the particular example of radiation therapy, before commencing treatment, a planning session (sometimes called a "simulation") is held, in order to plan the treatments and to determine the areas where the radiation will be delivered. The simulation session is generally conducted by a radiation oncologist, aided by one or more radiation therapists and often a dosimetrist, who performs the calculations and measurements necessary in the treatment planning. The simulation may last anywhere from fifteen minutes to an hour or more, depending on the complexity of the treatment.

During a simulation, a patient lies on a table, and a machine or a "simulator" is used to establish the areas, or "treatment fields," where radiation will be applied. The simulator is a tool that allows the radiation oncologist and therapist to observe the area to be treated, and the simulator's dimensions and movements closely match those of a linear accelerator. The simulation may, for example, be guided by fluoroscopy or CAT scan to observe the patient's internal anatomy, and the table upon which the patient rests can be raised and lowered, and rotated around a central axis.

During the simulation, marks are made on the patient's skin with magic markers, paint pens, or other suitable means (e.g., carbolfushin). These marks are very important because they enable precise and consistent positioning of the patient so as to ensure that the treatment radiation is properly directed to the appropriate treatment area, and the radiation therapist uses the marks in each subsequent session as a guide during the radiation treatment. The treatment plan and treatment fields prepared during the simulation session are verified, and radiation treatment is begun only after the radiation oncologist and therapists have confirmed the treatment field and calculations, and are satisfied with the setup.

Radiation therapy requires reproducibility over a number of days, weeks or even months, and the temporary marks must remain in positions established on the patient's skin after they are set during the simulation. However, given their temporary nature, such marks may be smudged, worn or erased after their initial application or between treatment sessions for a number of reasons, including washing or bathing, friction created by contact with a patient's clothing, or others. If the temporary marks are lost, the patient must undergo a new simulation in order to reestablish the treatment field and receive new temporary marks. Subsequent simulations are both inefficient and undesirable because they can waste time, money and resources, and unnecessarily prolong the treatment process.

Recent attempts to protect or maintain marks on a patient's skin have achieved limited success in overcoming the shortcomings of the prior art. For example, tiny permanent pinprick dots, sometimes called "tattoos," can be used in place of the temporary marks. Such permanent tattoos may be particularly advantageous in extended treatment periods because they may enable the therapist to set up treatment fields each day with precision, and the patient is allowed to wash and bathe without worrying about altering the treatment fields. However, there remain instances in which temporary marks are preferable to permanent tattoos. Such situations may include when a patient (e.g., a child) refuses to receive the pinprick associated with a permanent tattoo, or when the treatment field is highly visible (e.g., the patient's neck or face) and a permanent marking is not desirable. Additionally, the patient's skin color may make visibility of the tattoos difficult, and when it is likely that the treatment field will require subsequent modification, a permanent tattoo may not be appropriate. Moreover, unlike permanent tattoos, the use of temporary marks is largely unrestricted, as they provide greater ease, flexibility, freedom in use and margin for error in establishing treatment fields, and can be easily established or relocated. Temporary marks also may be shaped or sized as needed to effectively define a treatment field without permanently blemishing a patient's skin. Thus, it is often preferable to utilize temporary marks in establishing treatment areas or fields, and to attempt to cover or protect such marks from wear or erasure throughout the treatment cycle.

However, maintaining a temporary mark in place on a patient's skin over an extended period of time (e.g., over a multi-day or multi-week, such as a typical six-week, radiation treatment cycle) can be challenging. Some radiation therapists and facilities cover temporary marks using adhesive composites (e.g., Tegaderm®), tape, wound spray, stickers, or the like. For example, some radiation therapists use Tegaderm, which is commercially available in the form of framed sheets of predefined dimensions (e.g., approximately two inch by three inch sheets). In order to be more effectively used, these framed Tegaderm sheets generally must be manually cut and/or otherwise shaped by the radiation therapist, which can be time-consuming and inefficient. Additionally, once the associated frame is compromised, the Tegaderm material is not easily manipulated, because the material is very thin, and often wrinkles or folds over itself so that effective application is significantly inhibited. Similarly, the drawbacks associated with other conventional covering techniques are found in the handling of the covering materials, the application of the covering materials and/or the reliability or the lack of durability associated with the covering materials.

U.S. Patent Publication No. 2006/0111656 A1 to Broyles, which is assigned to the Assignee of the present invention, and is hereby incorporated by reference in its entirety as part of the present disclosure, discloses a temporary tattoo cover and related method. The cover comprises an opaque layer superimposed over an adhesive-backed transparent layer. The cover is applied to a mark, such as temporary tattoo on a person's skin, with the transparent layer adhered to the skin and overlying the mark to be covered. Once the cover is in place, the opaque layer is removed, and the transparent layer remains adhered to the skin and overlying the mark. However, one of the drawbacks associated with this type of cover is that the opaque layer covers the underlying transparent layer, and thus prevents the practitioner from easily viewing the underlying mark when applying the cover thereto. Another drawback associated with this type of cover is that the opaque layer is formed by two parts separated along a seam. In order to remove the opaque layer, the practitioner is required to pick at the seam in order to separate one half of the opaque layer from the other, and to then peel away the two halves of the opaque layer. At times, this process of removing the opaque layer can be more complicated and/or time consuming than otherwise desired.

It is an object of the present invention to overcome one or more of the above-described drawbacks and/or disadvantages of the prior art.

SUMMARY OF THE INVENTION

In accordance with a first aspect, the present invention is directed to a cover that is releasably attachable to a person's skin having thereon a temporary tattoo or other marking for covering the marking and allowing the underlying marking to be visible therethrough. The cover comprises a first flexible layer that is adhesively attachable to the person's skin over the temporary tattoo or other marking substantially without wrinkling. The first layer defines a first lower surface including an adhesive thereon that is releasably engageable by the adhesive with the person's skin in a position overlying the marking, an opposing first upper surface, and a substantially transparent portion that allows viewing of the underlying marking therethrough. A second layer is superimposed on the first layer. The second layer defines a second lower surface releasably adhered to the upper surface of the first layer, an opposing second upper surface, and a viewing window allowing viewing of the underlying marking through the second layer and the substantially transparent portion of the first layer. The second layer is sufficiently firm in comparison to the first layer to at least substantially maintain its shape under its own weight and the weight of the first layer.

In some embodiments of the present invention, the second layer extends about a peripheral region of the underlying first layer, and the viewing window extends throughout an inner portion of the second layer. In some such embodiments, the viewing window is defined by an aperture extending through the second layer. In some such embodiments, the second layer further defines a gap extending between the viewing window and a peripheral edge thereof. In some embodiments, the viewing window is defined by a first aperture, and the gap is defined by a second aperture formed through the second layer and extending between the peripheral edge and the first aperture. In some embodiments, the viewing window further defines a gap extending from an inner portion of the second layer to a peripheral edge thereof. In some embodiments of the present invention, the second layer is substantially opaque, and the first layer is substantially transparent throughout.

In some embodiments of the present invention, the cover defines an oblong peripheral shape and the viewing window defines a substantially linear, axially elongated shape. In some such embodiments, the cover defines two elongated, approximately straight edges located on opposites sides of the cover relative to each other, and two curvilinear edges located on opposite ends of the cover relative to each other and extending between the opposing elongated edges. In some such embodiments, the viewing window is defined by an axially elongated aperture extending approximately parallel to the opposing approximately straight edges from proximate one curvilinear edge to at least proximate the other curvilinear edge. In some such embodiments, the viewing window forms a gap extending through one of the curvilinear edges. In other embodiments of the present invention, the cover defines a substantially curvilinear peripheral shape and the viewing window defines a substantially curvilinear shape in an approximately central portion thereof. The covers may define any of a variety of shapes, including without limitation a substantially circular shape, a substantially oval shape, a substantially rectangular shape, a substantially oblong shape, a substantially curvilinear shape, a substantially elliptical shape, and a substantially rectilinear shape.

In accordance with another aspect, the present invention is directed to a device including a plurality of covers, and a continuous carrier substrate defining an uninterrupted releasable surface thereon. The plurality of covers are axially spaced relative to each other on the releasable surface of the carrier substrate, and each adhesive lower surface is releasably superimposed on the releasable surface of the carrier substrate. Preferably, the first and second layers of each cover define a predetermined peripheral shape and a maximum diameter or width that is sufficiently small to manually grip and remove the respective cover from the releasable surface of the carrier strip and, in turn, manually adhere the first layer to the person's skin in a position overlying the marking without substantially wrinkling the first layer.

In accordance with another aspect, the present invention is directed to a cover that is releasably attachable to a person's skin having thereon a temporary tattoo or other marking for covering the marking and allowing the underlying marking to be visible therethrough. The cover comprises first means for releasably and conformably attaching to the person's skin over the temporary tattoo or other marking substantially without wrinkling in a position overlying the marking and for allowing the underlying marking to be visible therethrough. The cover further includes second means superimposed on and releasably attached to the first means for substantially maintaining its shape under its own weight and the weight of the first means, and for releasably attaching the first means to the person's skin over the marking substantially without wrinkling the first means. Third means are provided for allowing viewing of the underlying marking through the second means.

Some embodiments of the present invention further include fourth means for facilitating manually engaging the second means and removing the second means from the first means after releasably attaching the first means to the skin. In some embodiments of the present invention, the first means is a first substantially transparent, flexible, adhesive backed layer; the second means is a second substantially opaque, relatively firm layer in comparison the first layer; the third means is a viewing window formed on the second layer; and the fourth means is a gap formed in the second layer and extending between the viewing window and a peripheral edge thereof.

In accordance with another aspect, the present invention is directed to a method for releasably attaching a cover to a person's skin having thereon a temporary tattoo or other marking for covering the marking and allowing the underlying marking to be visible therethrough. The method comprises the following steps:

(i) providing a cover including a first, flexible, adhesive-backed layer having at least a portion thereof that is substantially transparent, and a second layer superimposed on the first layer and including a viewing window;

(ii) viewing the underlying marking through the viewing window of the second layer and the substantially transparent portion of the first layer;

(iii) manually placing the adhesive-backed surface of the first layer of the cover onto the person's skin;

(iv) manually pressing the first layer of the cover toward the skin and, in turn, adhesively attaching the first layer of the cover to the skin without substantially wrinkling the first layer; and (v) removing the second layer from the first layer.

The method preferably further comprises substantially aligning the underlying marking with the viewing window; and manually placing the adhesive-backed surface of the first layer of the cover onto the person's skin in the substantially aligned position overlying the marking. Some embodiments of the present invention further comprise providing a second layer of the cover defining a gap extending between the viewing window and a peripheral edge of the cover, and manually engaging the peripheral edge of the second layer adjacent to the gap and removing the second layer from the first layer adhesively attached to the skin.

Some embodiments of the present invention further comprising the following steps:

positioning the person with respect to a simulation machine suitable to establish one or more radiation treatment fields;

setting at least one treatment field via the simulation machine;

utilizing at least one marking made on the patient's skin to position the patient for treatment; and adhesively attaching the first layer of at least one cover in a position overlying the respective marking.

Some embodiments of the present invention further comprise (i) providing a cover defining an axially elongated viewing window, and substantially aligning the axially elongated viewing window with a linear marking; and/or (ii) providing a cover defining a curvilinear viewing window, and substantially aligning an approximately central portion of the viewing window with an approximately central portion of the marking.

One advantage of certain embodiments of the present invention is that the viewing window allows the underlying tattoo or other marking to be viewed through the cover, and thus facilitates properly aligning the cover with the underlying tattoo or other marking. Another advantage of such currently preferred embodiments of the present invention, is that second layer is formed in one piece, and the gap in the second layer facilitates the ability of a practitioner to manually grip the second layer and remove the second layer after the first layer is adhesively attached to the skin. Yet another advantage of such embodiments of the present invention is that the second layer facilitates the ability to adhesively attach the first layer to the skin substantially without wrinkling thereof.

In accordance with another aspect, the present invention is directed to a cover that is releasably attachable to a patient's skin having thereon a temporary tattoo or other marking identifying a set-up point for radiation therapy. The cover overlies the temporary tattoo or other marking and allows the temporary tattoo or other marking to be visible therethrough. The cover comprises a flexible layer having a width or a diameter, shape, and thickness, and formed of a material, that, in combination, provide the flexible layer with characteristics that enable the flexible layer to be handled and adhesively attachable to the patient's skin over the temporary tattoo or other marking substantially without the flexible layer wrinkling during handling and attaching to the patient's skin for identifying a set-up point for radiation therapy. The flexible layer comprises a lower surface and an opposing upper surface. The cover further comprises an adhesive which covers substantially the entire lower surface and is releasably engageable with the patient's skin in a position overlying the temporary tattoo or other marking. The adhesive and the flexible layer are substantially transparent and allow viewing of the temporary tattoo or other marking therethrough. The flexible layer includes indicia in the form of crosshairs printed on the upper surface of the flexible layer and outside the adhesive layer. Inner ends of the crosshairs are spaced relative to each other and define a substantially transparent portion therebetween, and are configured to enable viewing the temporary tattoo or other marking through the substantially transparent portion during placement of the cover over the temporary tattoo or other marking.

In accordance with a further aspect, the present invention is directed to an apparatus including a plurality of covers that are releasably attachable to a portion of a patient's skin having thereon a temporary tattoo or other marking identifying a set-up point for radiation therapy and for covering the marking and allowing the temporary tattoo or other marking to be visible therethrough. The apparatus comprises a carrier substrate defining a releasable surface thereon. A plurality of covers comprising relatively flexible layers are spaced without touching each other on the releasable surface of the carrier substrate. Each flexible layer is substantially transparent and has an upper surface, an opposing adhesive lower surface releasably superimposed on the releasable surface, and a width or a diameter, shape, and thickness, and formed of a material, that, in combination, provide the flexible layer with characteristics that enable the flexible layer to be 1) removable from the releasable surface without substantially wrinkling; and 2) attachable to the patient's skin with substantially the entire adhesive lower surface adhesively engaging the skin substantially without wrinkling. The flexible layer engages the skin in a position with the lower and upper surfaces overlying the temporary tattoo or other marking and allowing the temporary tattoo or other marking to be visible through the substantially transparent flexible layer for identifying a set-up point for radiation therapy. Each cover includes indicia in the form of crosshairs printed on the upper surface of the flexible layer and outside of the adhesive lower surface. Inner ends of the crosshairs are spaced relative to each other and define a substantially transparent central portion therebetween and are configured to enable viewing the temporary tattoo or other marking through the substantially transparent central portion during placement of the cover over the temporary tattoo or other marking.

In accordance with yet a further aspect, the present invention is directed to an apparatus including a plurality of covers that are releasably attachable to a portion of a person's skin having thereon a temporary tattoo or other marking identifying a set-up point for radiation therapy for covering the temporary tattoo or other marking and allowing the temporary tattoo or other marking to be visible therethrough. The apparatus comprises a continuous carrier strip defining an uninterrupted releasable surface thereon. A plurality of first means are axially spaced relative to and without touching each other on the releasable surface of the carrier strip with the uninterrupted releasable surface of the carrier strip extending between adjacent first means. Each first means is for releasing from the releasable surface without wrinkling, for flexible and removable adhesive attachment on a lower side thereof to the person's skin in a position overlying the temporary tattoo or other marking substantially without wrinkling thereof, and for being substantially transparent for allowing the temporary tattoo or other marking to be visible therethrough for identifying a set-up point for radiation therapy. Each first means includes second means printed on an upper side thereof outside the lower side for adhesive attachment for locating the temporary tattoo or other marking visible through the substantially transparent first means. The second means includes inner ends spaced relative to each other and configured to enable viewing the temporary tattoo or other marking through a substantially transparent portion between the inner ends during placement of the cover over the temporary tattoo or other marking.

In accordance with another aspect, the present invention is directed to releasably attaching a cover to a patient's skin having thereon a temporary tattoo or other marking identifying a set-up point for radiation therapy, for covering the temporary tattoo or other marking, and allowing the temporary tattoo or other marking to be visible therethrough. The cover comprises a flexible layer having a width or a diameter, shape, and thickness, and formed of a material, that, in combination, provide the flexible layer with characteristics that enable the flexible layer to be handled and adhesively attachable to the patient's skin over the temporary tattoo or other marking substantially without the flexible layer wrinkling during handling and attaching to the patient's skin. The cover is releasably engageable with the patient's skin in a position overlying the temporary tattoo or other marking. The flexible layer has a lower surface and an opposing upper surface. An adhesive covers substantially the entire lower surface. The adhesive and the flexible layer are substantially transparent and allow viewing of the temporary tattoo or other marking therethrough. The flexible layer includes indicia in the form of crosshairs printed on the upper surface of the flexible layer and outside the adhesive layer. Inner ends of the crosshairs are spaced relative to each other to define a substantially transparent portion therebetween, and are configured to enable viewing the temporary tattoo or other marking through the substantially transparent portion during placement of the cover over the temporary tattoo or other marking. Attaching the cover includes the steps of (i) viewing the temporary tattoo or other marking for identifying a set-up point for radiation therapy through the substantially transparent portion;

(ii) substantially aligning the substantially transparent portion between the inner ends of the crosshairs with the temporary tattoo or other marking; and (iii) placing the adhesive-containing lower surface of the flexible layer of the cover onto the patient's skin and, in turn, adhesively attaching the flexible layer of the cover to the skin without substantially wrinkling the flexible layer and with the temporary tattoo or other marking visible through the substantially transparent portion between the inner ends of the crosshairs.

These and other advantages of the present invention, and/or of the currently preferred embodiments thereof, will become more readily apparent in view of the following detailed description of the currently preferred embodiments and accompanying drawings.

DETAILED DESCRIPTION OF PREFERRED EMBODIMENTS

In FIGS. 1 through 5, a temporary tattoo cover embodying the present invention is indicated generally by the reference numeral 110. The cover 110 is particularly appropriate for covering and protecting marks made on the skin, for example, in preparation for radiation therapy. However, the cover 110 herein described may be used in any application wherein a marking is made to a person's skin, and wherein it is desired to protect the marking from wear, removal or erasure caused by interaction with water, friction, other external elements or any other source.

As is shown in FIGS. 1 through 5, the cover 110 comprises a first or underlying layer 112 and a second or overlying layer 120. The first layer 112 comprises a first upper surface 114, a first lower surface 116, and a first peripheral edge 118. The first layer 112 is sufficiently transparent or translucent to allow viewing of an underlying tattoo or other marking therethrough. Like the first layer 112, the second layer 120 comprises a second upper surface 122, a second lower surface 124, and a second peripheral edge 126. The second layer 120 further defines a viewing window 128, which in the illustrated embodiment is defined by an aperture formed through the second layer. The second layer 120 further defines a gap 132 that extends laterally from the window 128 to the second peripheral edge 126, and the gap 132 forms two opposing edges radially spaced relative to each other to facilitate manually engaging and removing the second layer 120 from the first layer 112, as is described further below.

During operation, the cover 110 may be applied over a skin mark of any kind. A user may orient the cover 110 over the mark by sighting the mark through the transparent first layer 112 and the window 128 of the second layer 120, and affixing the cover 110 to the person's skin. The first layer 112 adhesively attaches to the person's skin over and around the mark, substantially without wrinkling the first layer, the underlying skin or the mark itself. Once the cover 110 is appropriately positioned over the mark, the second layer 120 is removed, and the first layer 112 remains in place over the marking.

As is shown in FIGS. 1 through 5, the first layer 112 is defined by a first peripheral edge 118 and two substantially planar surfaces: a first lower surface 116, which contacts the skin with an adhesive coating thereon, and an opposing first upper surface 114, which releasably adheres to the second lower surface 122 of the second layer 120. In the illustrated embodiment, the planar surfaces 114, 116 and the first peripheral edge 118 of the first layer 112 form a substantially circular or disc-like shape. However, as may be recognized by those of ordinary skill in the pertinent art based on the teachings herein, the covers of the present invention may define any of numerous different shapes or configurations that are currently known, or that later become known.

The first layer 112 preferably conforms to anatomical surfaces by flexibly conforming in a complementary fashion with the underlying skin. Although the first layer 112 may be formed from a variety of different materials and/or composites, particularly well-suited materials for use in forming the first layer 112 include elastomeric polyurethane films or the like, which provide the preferred properties of resiliency, high moisture vapor permeability and at least substantial transparency or translucency, and do not irritate the underlying skin. Examples of suitable commercially available materials for use in forming the first layer 112 include 3M 9841 and 3M 9832 polyurethanes available from Minnesota Mining and Manufacturing Co., which are thin, hypoallergenic, fluid resistant, transparent and conformable to various anatomical surfaces. The first layer 112 also may be a composite of two or more sub-layers, such that the first upper surface 114 is defined by one sub-layer providing specific material characteristics while the first lower surface 116 of the second layer 120 is defined by another sub-layer providing the same or different material characteristics. For example, 3M 9841 polyurethane and 3M 9832 polyurethane may be laminated together to form a composite first layer 112.

The adhesive suitable for use with the first lower surface 116 can be any conventional adhesive typically used in skin-contacting applications. Exemplary adhesives are disclosed in U.S. Pat. Nos. Re. 24,906, 3,389,827, 4,112,213, 4,310,509, 4,323,557, and 4,737,410. One suitable adhesive transmits moisture vapor at a rate greater than or equal to that of human skin. Additionally, the adhesive on the first lower surface 116 also permits the cover 110 to be mounted on a releasable backing and protected during non-use. The backing materials may include without limitation any of numerous different paper-based products, polypropylene, polyethylene, polyester or any combination of these materials. The releasable backings facilitate transportation and storage when the cover 110 is not in use. If desired, one or more covers 110 may be stored in sheets or rolls, and adapted for ready dispensation when needed.

The first upper surface 114 of the underlying layer 112 is preferably free of adhesives. However, if desired, the first upper surface 114 may be provided with a low-adhesion coating, such as a solution of polyvinyl n-octadecyl carbamate, as disclosed, for example, in U.S. Pat. No. 2,532,011. However, it will be readily understood by those skilled in the pertinent art that any of a variety of other coatings that are suitable for providing appropriate low-adhesion properties or a low-adhesion bond equally may be used.

As is shown in FIGS. 1 through 5, the second layer 120 is defined by a second peripheral edge 126 and two substantially planar surfaces: a second lower surface 124, which releasably adheres to the first upper surface 114, and an opposing second upper surface 122. The second layer 120 also defines the substantially centrally located viewing window 128, and the gap 132 extending from the window 128 to the second peripheral edge 126. The gap 132 provides greater visibility for aligning marks while placing the cover 110 into position, and facilitates the removal of the second layer 120 from the first layer 112 once the cover is applied to a person's skin, preferably enabling a user to peel back the second layer 120 from the first layer 112. Although the viewing window 128 is substantially circular, and the gap 132 is substantially straight and extends radially between the viewing window 128 and peripheral edge 126, these features may take any of numerous different shapes and/or configurations that are currently known or that later become known. For example, the gap 132 may be curvilinear, or the second layer 120 may define plural gaps or may not define any gaps at all. The inclusion of the gap and/or the characteristics thereof may be selected based on any of a variety of factors, such as the size and location of the mark on the person's skin, the intended therapy or procedure to be performed, or any other criteria.

Also in the illustrated embodiment, the surfaces 122, 124 and the second peripheral edge 126 of the second layer 120 define a second substantially circular or disc-like shape, and the window 128 is also substantially circular. As may be recognized by those of ordinary skill in the pertinent art based on the teachings herein, the window may take any of numerous different shapes and/or configurations that are currently known or that later become known. For example, the shape of the window 128 may be varied to accommodate skin marks of various sizes and shapes. In addition, the window 128 may encompass any proportion of the second layer 120, based on the desired use of the cover 110 or other factors.

The second layer 120 is preferably substantially stiffer than, or relatively rigid in comparison to, the first layer 112, and preferably cooperates with the first layer 112 so as to maintain the integrity of the cover 110 during both handling and application. Suitable materials for use in forming the second layer 120 include, but are not limited to, silicone-coated papers, polyethylene/vinyl acetate copolymer-coated papers and polyester or polyurethane films. Those skilled in the pertinent art will readily recognize from the present disclosure that any of a variety of other materials and/or combinations thereof equally may be utilized in forming the second layer 120.

The first upper surface 114 and the second upper surface 122 may be suitable for printing, so as to allow information to be communicated thereon. For example, product information may be provided on the first upper surface 114 so as to allow for ready recognition of the product source (e.g., a trademark). Additionally, drawings, sketches or alphanumeric characters may be provided on either the first upper surface 114 or the second upper surface 122 for any purpose, such as to comfort a wearer, especially a child, during the medical procedure.

In addition to letters, numbers, prints and the like, the first layer 112 and/or the second layer 120 may be marked with any of various indicia, including rings, lines or portions thereof, to aid the user in locating the mark prior to applying the cover 110 to the person's skin, aligning the window and/or cover with the underlying marking, and/or to aid a subsequent user in locating a marking beneath a cover that already has been applied to the person's skin. Such indicia may include crosshairs, rings, concentric rings, or portions thereof, or any other markings for a variety of purposes that are currently known, or that later become known. For example, the exemplary variation of the cover of FIG. 3 comprises crosshairs 134 that are printed on the first layer 112 and intersect at the approximate center of the first layer within the window 128. Indicia such as crosshairs 134 may be used to accurately position the cover 110 over a marking on a person's skin to align the window and cover with the underlying marking, and also aid in locating the covered marking during treatment. If desired, the crosshairs 134 or other indicia may be applied to one or both of the underlying and overlying layers. In addition, the color or type of indicia may be selected based on a number of factors, including the color or tone of the person's skin; the color, type, or style of marking to be covered; or the application for which the cover 110 is to be used. For example, dark-colored indicia may be printed on a first layer 112 which is intended to be applied to a temporary mark on a fair-skinned person (i.e., the indicia is darker than the person's skin to visually contrast therewith), whereas relatively light-colored indicia, such as white, yellow, green, turquoise, bright versions of the foregoing colors, and/or fluorescent-colored indicia, may be printed on a cover 110 which is intended for use on a person with darker skin (i.e., the indicia is lighter and/or brighter than the person's skin to visually contrast therewith). In one such embodiment, indicia in the form of a "plus sign" (i.e., "+") is printed on the underlying layer within the viewing window, and the color of the indicia is white, lime green, or other light, bright, or fluorescent color, for enhancing the visual contrast between the indicia and relatively dark skin, such as brown or black. Accordingly, one advantage of such embodiments of the present invention is that the coloration of the indicia on the first or underlying layer that is adhesively attached to the skin is selected to contrast with the color of the skin to facilitate viewing the marking, or the indicia of the cover overlying the marking, and to visually distinguish the marking, or the indicia aligned with and covering the marking, from the surrounding skin, during, for example, a radiation therapy treatment.

In the illustrated embodiment, the second peripheral edge 128 is substantially coincident or coterminal with the first peripheral edge 118 of the first layer 112, corresponding to the substantially equal sizes of the first layer 112 and the second layer 120. However, the second peripheral edge 128, or a portion thereof, such as a portion forming a tab, may extend beyond the first peripheral edge 118, so as to facilitate the manual removal of the second layer 120 from the first layer 112. For example, a portion of the second layer 120 may form a tab or other extension which enables a user to easily remove the cover 110 from a releasable backing prior to application, and also to remove the second layer 120 from the first layer 112 after the cover 110 has been applied.

The second lower surface 124 of the second layer 120 may be provided with a low-adhesion coating such as, for example, a solution of polyvinyl n-octadecyl carbamate as disclosed, for example, in U.S. Pat. No. 2,532,011, for effectuating an appropriate bond between the first upper surface 114 of the first layer 112 and the second lower surface 124 of the second layer 120. It will be readily apparent to those skilled in the pertinent art from the present disclosure that any of a variety of other coatings suitable for providing appropriate low-adhesion properties equally may be used. In addition, as indicated above, the first upper surface 120 of the first layer 112 also may be provided with any of a variety of different adhesives for purposes of accomplishing any of a variety of objectives.

The bond between the second lower surface 124 and the first upper surface 114 is preferably stronger than the bond between the first lower surface 116 and a releasable backing that may be provided to store or transport the cover 110 when not in use. This difference in bond strength preferably ensures that the second layer 120 remains adhered to the first layer 112 when the cover 110 is removed from such backing. Conversely, the bond between the first lower surface 118 and a person's skin is preferably stronger than the bond between the second lower surface 124 and the first upper surface 120, ensuring that the first layer 112 will remain in place on the person's skin when the second layer 120 is removed.

In the illustrated embodiment, the first layer 112 and second layer 120 are of substantially equal thickness. Preferably, the first layer 112 has a thickness of about 0.02 millimeters to about 0.04 millimeters, while the second layer 120 has a thickness of about 0.02 millimeters to about 0.08 millimeters, although the thicknesses of the first layer 112 and second layer 120 may be modified for different applications or purposes as desired. Because the second layer 120 is preferably more rigid than the first layer 112, a user may manipulate the entire cover 110 by grasping about the second peripheral edge 126 without compromising the integrity of the first layer 112, prior to and during application of the cover 110 to a person's skin with or without the use of additional structures (e.g., tabs). This arrangement maintains the integrity of the first layer 112 via the relative rigidity of the second layer 120 during both handling and application, because the first layer 112 is prevented from becoming folded, wrinkled or otherwise compromised by the second layer 120 when the cover 110 is removed from its backing for positioning and ultimate application to a person's skin. Consequently, the arrangement also provides for an improved adhesion between the first layer 112 and the person's skin, as wrinkles, creases, punctures and/or other adhesion imperfections are substantially reduced or eliminated. In substantially circular or like curvilinear embodiments of the cover 110, the first layer 112 and the second layer 120 preferably define a width or diameter within the range of about 10 millimeters to about 40 millimeters, and more preferably within the range about 20 millimeters to about 30 millimeters. However, the dimensions of the cover 110 of the present invention may be modified for different applications or purposes as desired.

Figure 1:
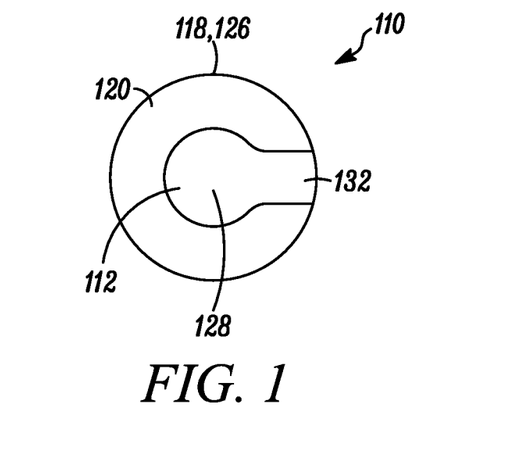
FIG. 1 is a top plan view of a first embodiment of a temporary tattoo cover of the present invention defining a substantially circular shape.
Figure 2:
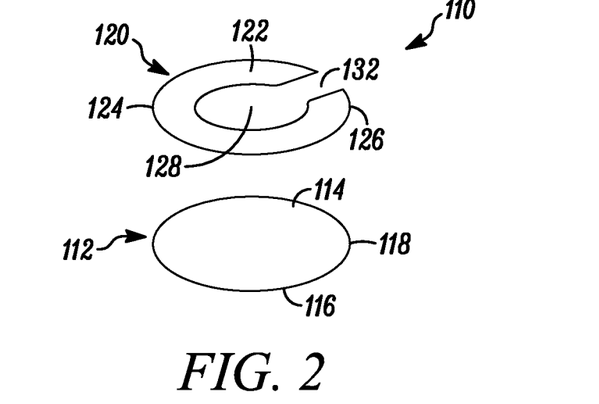
FIG. 2 is an exploded perspective view of the temporary tattoo cover of FIG. 1 showing the underlying transparent layer, and the overlying ring-shaped opaque layer defining an approximately central viewing window and a gap extending between the viewing window and a peripheral edge to facilitate manually engaging the overlying layer.
Figure 3:
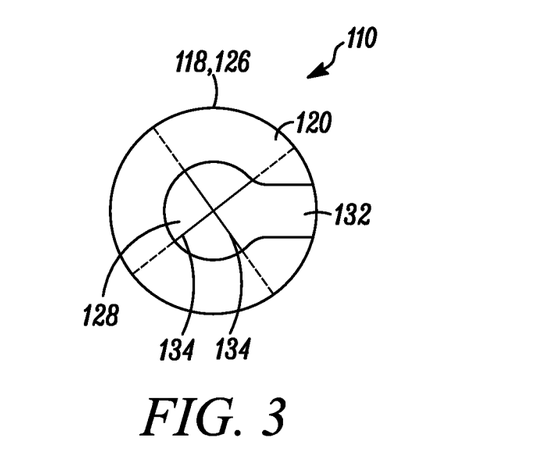
FIG. 3 is a top plan view of an exemplary variation of the temporary tattoo cover of FIG. 1 including crosshairs marked on the underlying transparent layer that may be aligned with an underlying tattoo or other marking on the person's skin.
Figure 4:
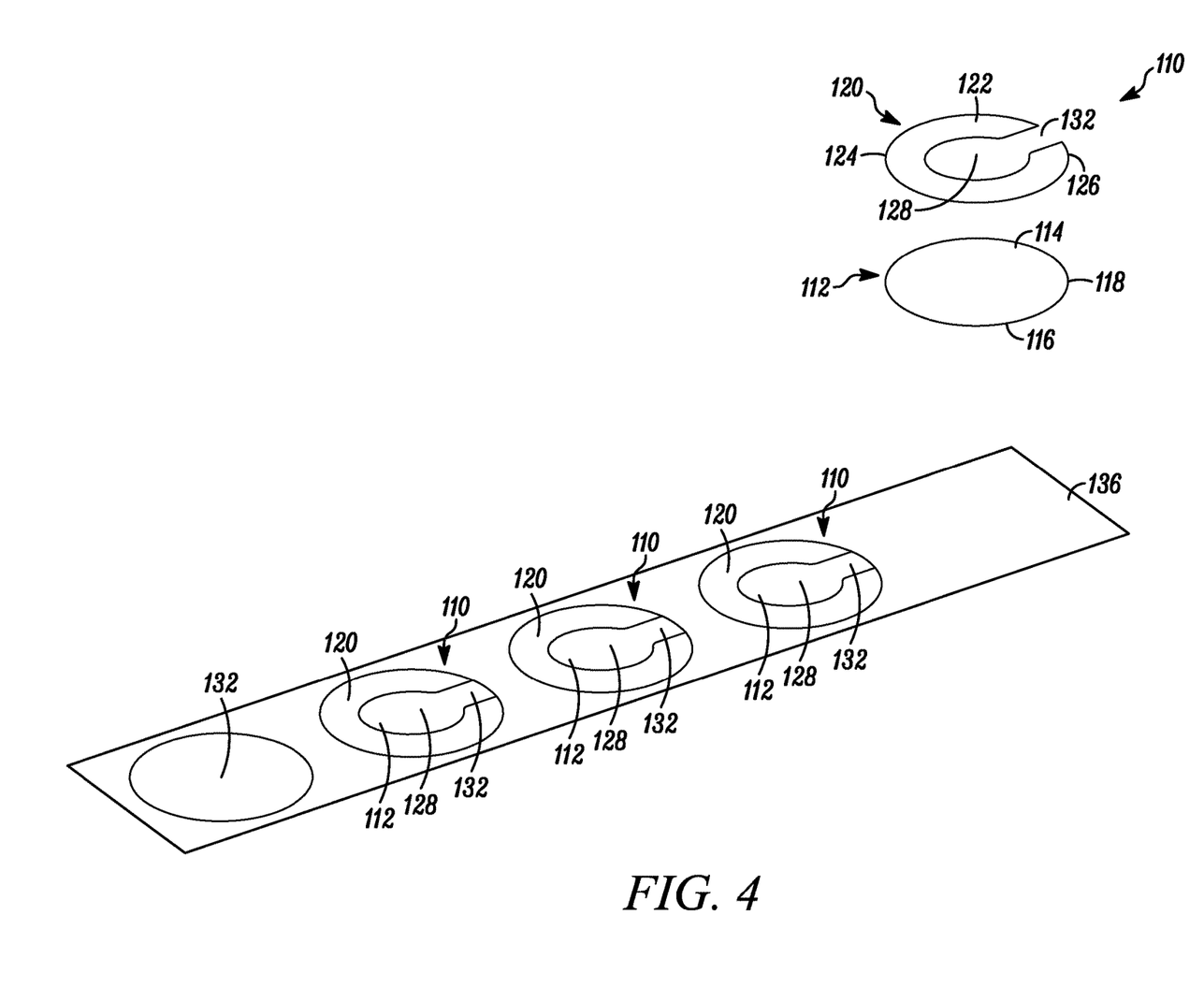
FIG. 4 is a perspective view of a plurality of the temporary tattoo covers of FIG. 1 axially spaced relative to each other on an axially-elongated, releasable substrate provided in strip form, such as on a roll, and showing an exploded view of one cover.
Figure 5:
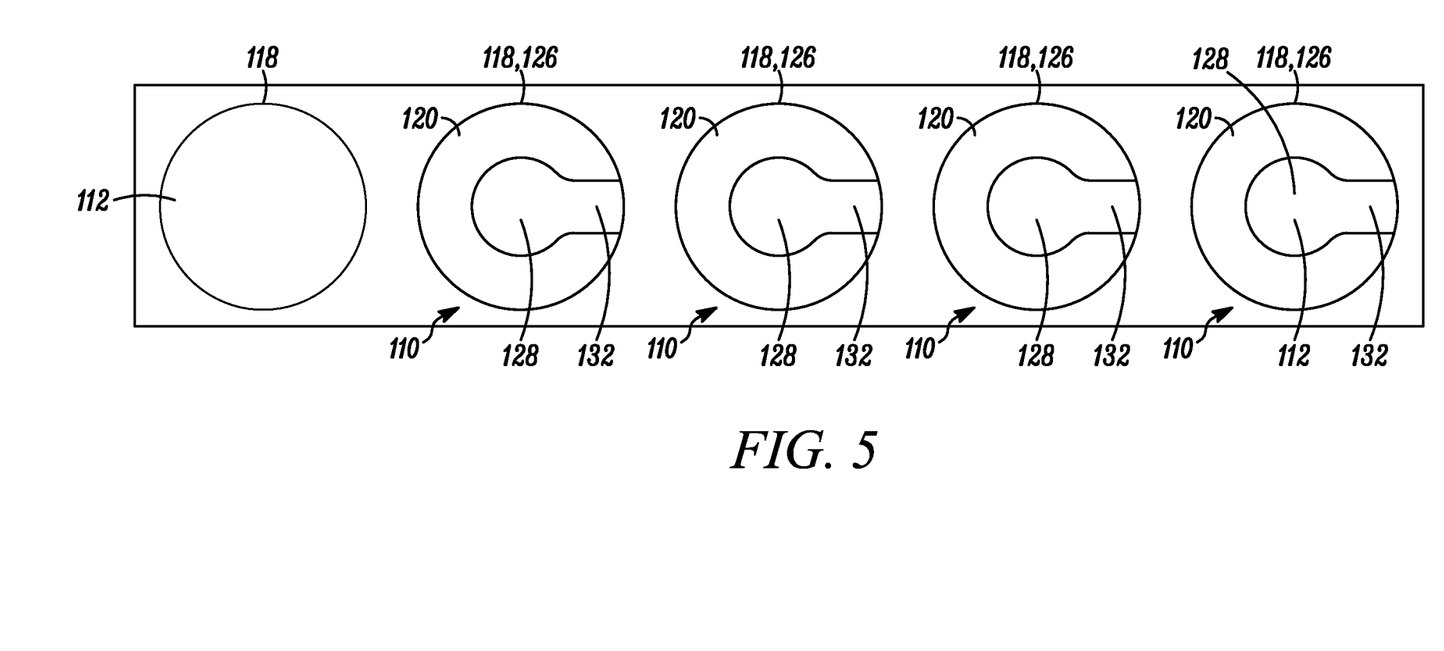
FIG. 5 is a top plan view of the plurality of temporary tattoo covers of FIG. 4 on the releasable substrate.

As is shown in FIGS. 4 and 5, the adhesive on the first lower surface 116 of the first layer 112 permits the cover 110 to be affixed to a releasable backing material during storage or transportation, such as an axially-elongated substrate 136. If desired, a single cover 110 may be applied to a single respective backing, or plural covers 110 may be applied to the same backing, which may be stored in a sheet-like form, rolled or otherwise maintained for ready dispensation and use. Preferably, the backing may be a continuous carrier substrate 136 defining a releasable surface thereon, with a plurality of covers 110 axially spaced relative to each other on the releasable surface of the continuous carrier substrate 136. More preferably, the first and second layers of each cover 110 define a predetermined peripheral shape and a maximum width that is sufficiently small to manually grip and remove a cover 110 from the substrate 136, and manually apply the first layer 112 to a person's skin. Further, the sheet-like form may enable mass production of covers 110 through, for example, mechanical processes which apply the first layer 112 and the second layer 120 to a substrate 136 in a series of operations, or all at once.

Although the covers 110 described in FIGS. 1 through 5 are substantially circular, the scope of the present invention is not limited to such embodiments, and other shapes may be used. The covers of the present invention may take any of numerous different shapes that are currently known, or that later become known, including without limitation, substantially rectangular, substantially oblong, substantially oval, substantially triangular, or any other curvilinear or rectilinear shape. Criteria for selecting the shape of the cover may include the size and location of the mark on the person's skin, the intended therapy or procedure to be performed, and others. In the context of radiation therapy, substantially circular covers (such as those shown in FIGS. 1 through 5) may be appropriate for covering three-point set-ups, isocenters, corners of field borders, or match lines.

Figure 6:
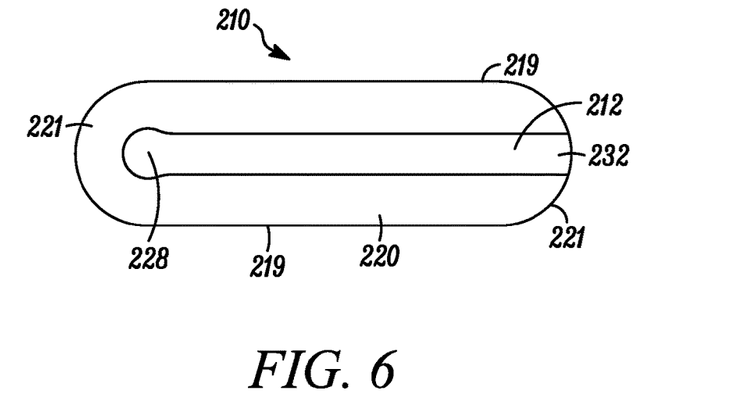
FIG. 6 is a top plan view of another embodiment of a temporary tattoo cover of the present invention defining an oblong shape, and including an axially-elongated viewing window that is particularly suitable for viewing and alignment with elongated, such as linear shaped, temporary tattoos or other markings.
Figure 7:
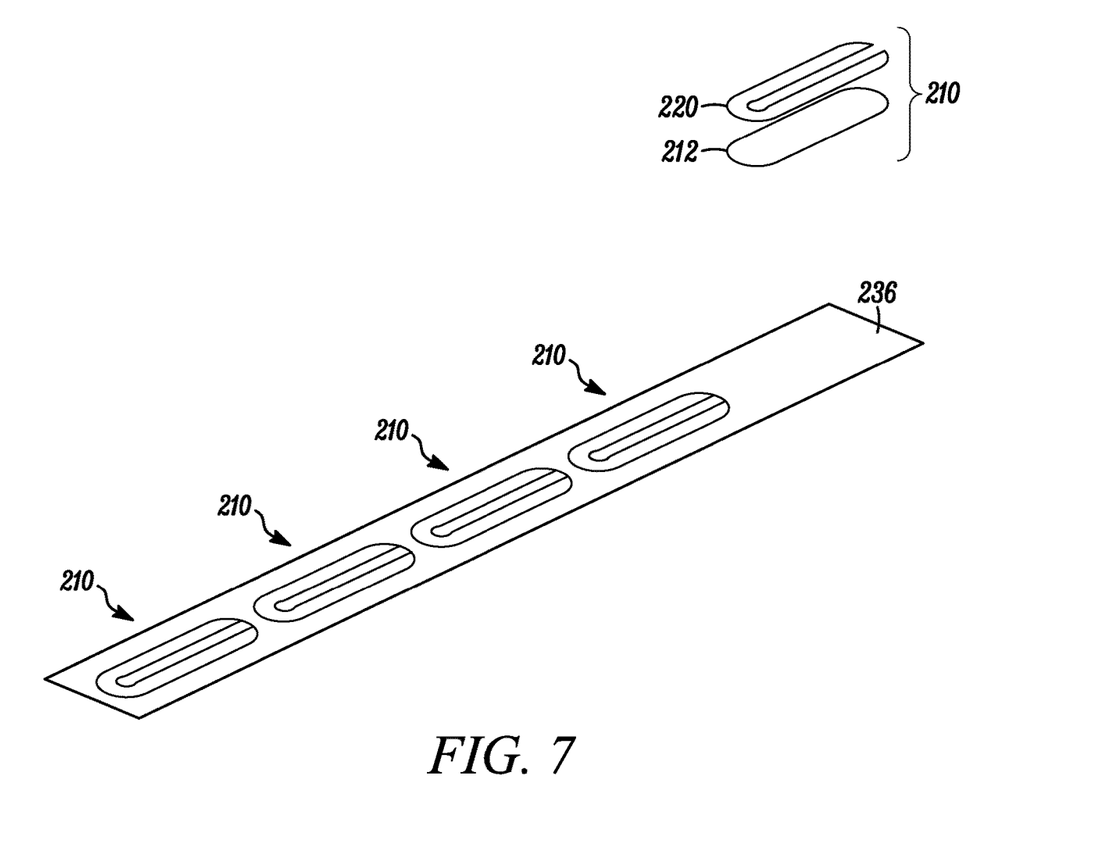
FIG. 7 is a perspective view of a plurality of the temporary tattoo covers of FIG. 6 axially spaced relative to each other on an axially-elongated, releasable substrate provided in strip form, such as on a roll, and showing an exploded view of one cover.

Turning to FIGS. 6 and 7, another embodiment of a cover of the present invention is indicated generally by the reference numeral 210. The cover 210 is substantially similar to the cover 110 described above, and therefore like reference numerals preceded by the numeral "2" instead of the numeral "1" are used to indicate like elements.

The primary difference of the cover 210 in comparison to the cover 110 described above, is that the cover 210 is oblong shaped. More specifically, the cover 210 defines two elongated, approximately straight edges 219 located on opposites sides of the cover relative to each other, and two curvilinear edges 221 located on opposite ends of the cover relative to each other and extending between the opposing elongated edges 219. The viewing window 232 of the second or overlying layer 220 is defined by an axially elongated aperture extending approximately parallel to the opposing approximately straight edges 219 from proximate one curvilinear edge 221 to the opposite curvilinear edge 221 forming a gap extending through the edge.

The cover 210 may be applied to a person's skin and utilized in the same or substantially similar manner as the substantially circular cover 110 described above. However, the cover 210 may be more appropriate than the cover 110 when the mark to be covered is axially elongated or linear shaped. In the context of radiation therapy, a substantially oblong cover such as the cover 210 may be particularly appropriate for covering election breast borders, match lines, leveling lines or spine fields. Additionally, the cover 210 may define a width within the range of about 10 millimeters to about 40 millimeters, and more preferably within the range of about 30 millimeters to about 60 millimeters. However, as may be recognized by those of ordinary skill in the pertinent art, these dimensions are only exemplary, and any of numerous dimensions equally may be employed.

In practice, a radiation therapist or other user may preserve a mark by utilizing the cover 110 or the cover 210 of the present invention to cover a mark that was applied to a patient in preparation for treatment, such as during a simulation, thereby ensuring that the relevant treatment areas are consistently and properly maintained among different treatment sessions. Covers 110, 210 can be replaced as needed at any time during the therapy treatment period (e.g, at week three of a six-week treatment) so as to optimize the protective effect provided by such covers.

Figure 8:
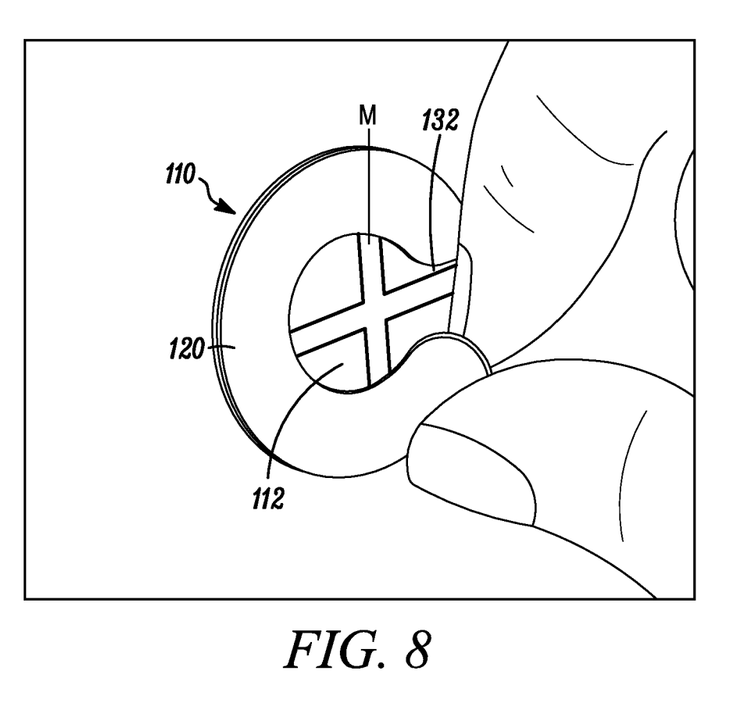
FIG. 8 is a perspective view of the temporary tattoo cover of FIG. 1 adhesively attached to a person's skin with an underlying cross-shaped marking "M" on the skin aligned with the viewing window, and showing a user's fingers manually engaging the overlying cover at the gap to remove the cover.
Figure 9:
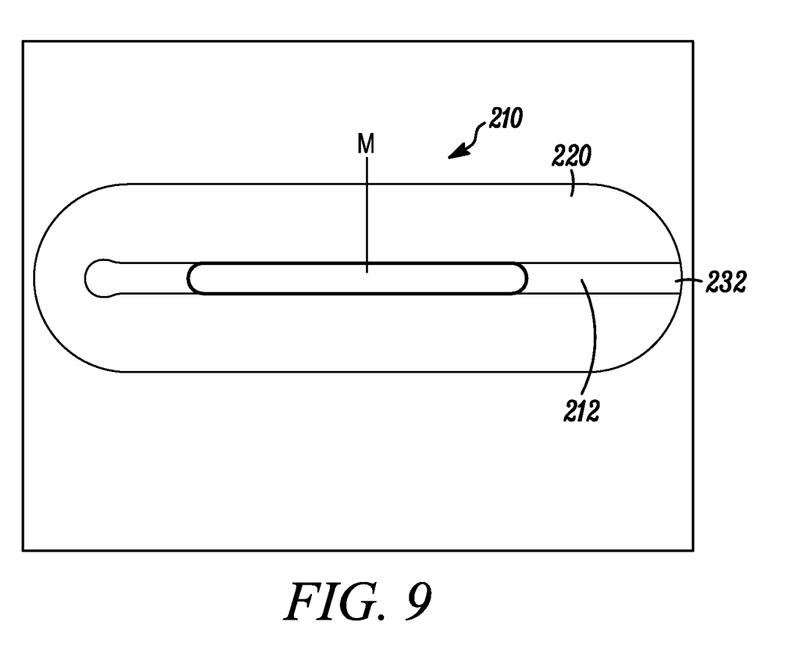
FIG. 9 is a perspective view of the temporary tattoo cover of FIGS. 6 and 7 adhesively attached to a person's skin with an underlying linear-shaped marking "M" on the skin aligned with the viewing window, and prior to manual engagement and removal of the overlying layer.

Thus, as shown typically in FIGS. 8 and 9, the currently preferred embodiments of the present invention are directed to a method for releasably attaching a cover 110, 210 to a person's skin having thereon a mark M thereon, for covering the mark M and allowing the underlying mark M to be visible therethrough. The method comprises (i) providing a cover 110, 210 including a first, flexible, adhesive-backed layer 112, 212 having at least a portion thereof that is substantially transparent or translucent, and a second layer 120, 220 superimposed on the first layer 112, 212 and including a viewing window 128, 228; (ii) viewing the underlying marking M through the viewing window 128, 228 of the second layer 120, 220 and the substantially transparent portion of the first layer 112, 212, and substantially aligning the underlying marking M with the viewing window 128, 228; (iii) manually placing the adhesive-backed surface of the first layer 112, 212 of the cover 110, 210 onto the person's skin in the substantially aligned position overlying the marking M; (iv) manually pressing the first layer 112, 212 of the cover 110, 210 toward the skin and, in turn, adhesively attaching the first layer 112, 212 of the cover 110, 210 to the skin without substantially wrinkling the first layer 112, 212; and (v) removing the second layer 120, 220 from the first layer 112, 212.

As described above, the second layer 120, 220 of the cover 110, 210 defines a gap 132, 232 extending between the viewing window 128, 228 and a peripheral edge 126, 226 of the cover 110, 210, and the method includes manually engaging the peripheral edge 126, 226 of the second layer 120, 220 adjacent to the gap 132, 232, as shown typically in FIG. 8, and removing the second layer 120, 220 from the first layer 112, 212 adhesively attached to the skin. Some embodiments further comprise the steps of positioning the person with respect to a simulation machine suitable to establish one or more radiation treatment fields; setting at least one treatment field via the simulation machine; utilizing at least one marking M made on the patient's skin to position the patient for treatment; and adhesively attaching the first layer 112, 212 of at least one cover 110, 210 in a position overlying the respective marking M. Some embodiments of the present invention may also comprise providing a cover 110, 210 defining an axially elongated viewing window 128, 228, and substantially aligning the axially elongated viewing window 228 with a linear marking M on a person's skin, or providing a cover 110, 210 defining a curvilinear viewing window 128, 228, and substantially aligning an approximately central portion of the viewing window 128, 228 with an approximately central portion of the marking M.

Thus, it will be readily understood by those of ordinary skill in the pertinent art from the present disclosure that the exemplary temporary covers disclosed herein, and corresponding methods of using such covers, are well suited for use in radiation therapy and other treatments. Indeed, the covers and methods of the present invention are well-suited for use in protecting temporary marks, such as temporary tattoos, on patients for an extended period of time during radiation therapy or other treatments. In addition, the covers equally may be used to cover, and facilitate identification of permanent marks, such as permanent tattoos, particularly in applications involving darker skin, such as brown or black skin. In such applications, the covers employing skin-color contrasting indicia, such as white or other relatively light or bright colored indicia as described above, are particularly advantageous with respect to facilitating identification of the permanent tattoo or other indicia.

Figure 10:
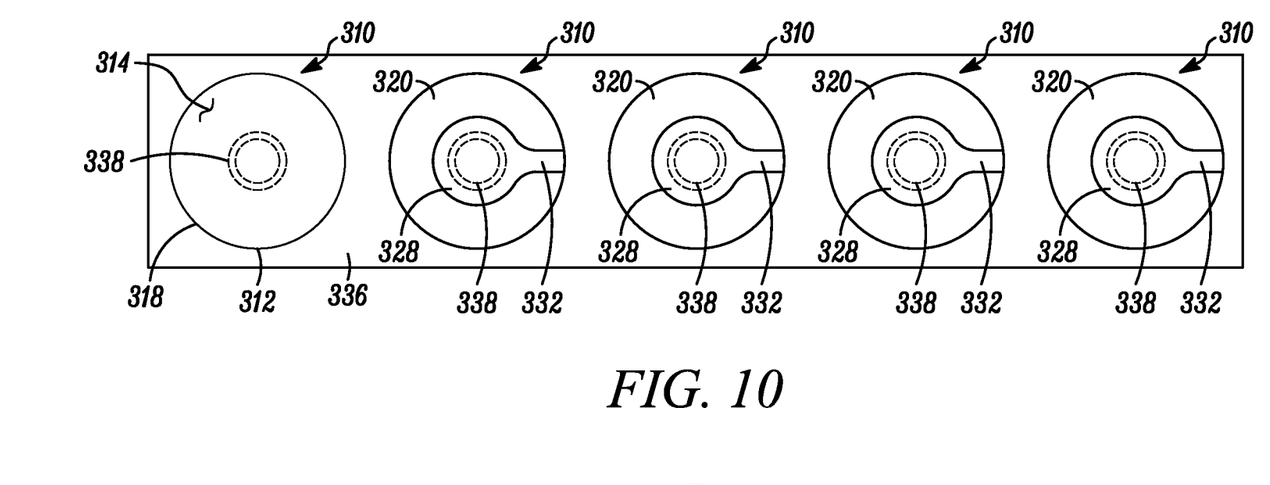
FIG. 10 is a top plan view of another embodiment of a temporary tattoo cover of the present invention including a printed circular indicia thereon to facilitate locating and aligning the cover with a temporary tattoo or other marking on the skin, and illustrating a plurality of such covers mounted on a strip including a releasable backing.

Turning to FIG. 10, another cover embodying the present invention is indicated generally by the reference numeral 310. The cover 310 is substantially similar to the cover 110 described above in connection with FIGS. 1 through 5, and therefore like reference numerals preceded by the numeral "3" instead of the numeral "1" are used to indicate like elements. The primary difference of the cover 310 in comparison to the cover 110 is that the cover 310 includes a circular indicia 338 printed on the central region of the first layer 314 to facilitate viewing therethrough an underlying marking, such as a temporary tattoo, and aligning the underlying marking with the circular indicia and thus the cover. As can be seen, a plurality of covers 310 are mounted on a strip 336 forming a releasable backing. On the far left of FIG. 10 the cover 310 is shown with the upper layer 320 removed to better illustrate the underlying layer 312. In the illustrated embodiment, the printed indicia 338 is substantially opaque, and preferably is defined by a relatively light or bright skin-contrasting color, such as white, yellow, green, turquoise, or combinations of these or other light or bright colors. Also in the illustrated embodiment, the remainder of the layer 312 is substantially transparent or translucent to allow viewing therethrough. Preferably, the inner diameter or width of the indicia is within the range of about ⅛ inch to about 3/16 inch, and the line thickness of the indicia is within the range of about 0.02 inch to about 0.1 inch. In the illustrated embodiment, the inner diameter of the circular indicia is about ¼ inch, and the line thickness of the indicia is about 0.04 inch. As may be recognized by those of ordinary skill in the pertinent art based on the teachings herein, the indicia may take any of numerous different shapes, sizes and/or line thicknesses that are currently known, or that later become known. One advantage of the circular or other annular shaped indicia is that they allow viewing the underlying marking through the central region of the indicia (i.e., the indicia does not interfere with viewing the underlying marking at the center of the cover) for purposes of aligning the indicia and cover with the marking. Yet another advantage of the currently preferred embodiments is that the coloration of the indicia significantly facilitates the viewing and marking alignment process, particularly with relatively dark skin, such as brown or black skin, applications.

Figure 11:
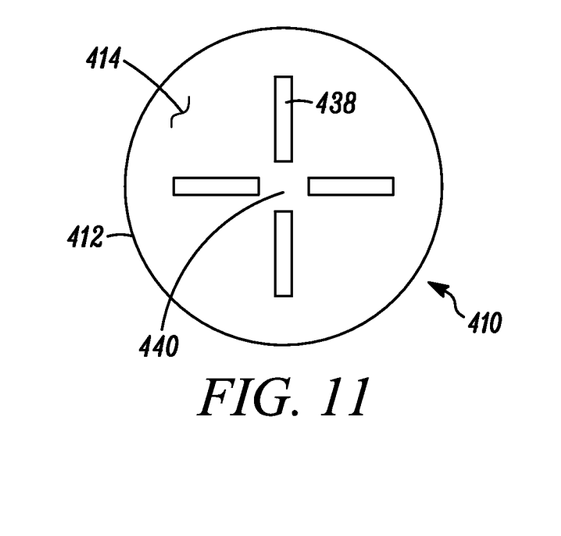
FIG. 11 is a top plan view of another embodiment of a temporary tattoo cover of the present invention including printed crosshairs thereon, wherein the inner ends of the crosshairs are spaced relative to each other to facilitate viewing an underlying temporary tattoo or other marking therethrough and aligning the crosshairs with the marking.

Turning to FIG. 11, another cover embodying the present invention is indicated generally by the reference numeral 410. The cover 410 is substantially similar to the cover 310 described above in connection with FIG. 10, and therefore like reference numerals preceded by the numeral "4" instead of the numeral "3" are used to indicate like elements. The primary difference of the cover 410 in comparison to the cover 310 is that the cover 410 includes indicia 438 in the form of crosshairs, wherein the inner ends of the crosshairs are radially spaced relative to each other to define an unobstructed central viewing region 440 located at the approximate center of the cover. The cover 410 is shown with the upper layer 420 removed to better illustrate the underlying layer 412. In the illustrated embodiment, the printed indicia (crosshairs) 438 is substantially opaque, and preferably is defined by a relatively light or bright skin-contrasting color, such as white, yellow, green, turquoise, or combinations of these or other light or bright colors. Also in the illustrated embodiment, the remainder of the layer 412 is substantially transparent or translucent to allow viewing therethrough. Preferably, the diameter or width of the central viewing region 440 is within the range of about ⅛ inch to about 3/16 inch, and the line thickness of the indicia is within the range of about 0.02 inch to about 0.1 inch. As may be recognized by those of ordinary skill in the pertinent art based on the teachings herein, the crosshairs or other indicia may take any of numerous different shapes, sizes and/or line thicknesses that are currently known, or that later become known. In addition, the crosshairs of other indicia may be applied to the upper layer instead of the lower layer, or may be applied to both layers.

As may be recognized by those of ordinary skill in the pertinent art based on the teachings herein, numerous changes and modifications may be made to the above-described and other embodiments of the present invention without departing from its scope as defined in the appended claims. For example, the viewing window formed in the second or overlying layer may be formed in any of numerous different ways that are currently known, or that later become known, such as by forming an aperture through the second layer as described above, or by forming the second layer in whole or in part of a transparent or translucent material to define a transparent or translucent window. The term "transparent" is used herein to include any level of transparency that is sufficient to allow viewing of the underlying marking through the window, and includes without limitation, completely transparent, partially transparent, or translucent. The term "temporary tattoo" or "tattoo" is used herein to mean without limitation any type of marking applied to person's skin that is to be covered, including a marking applied by a marking pen, such as a Sharpie® pen, in any of numerous different shapes or configurations, that are currently known, or that later become known. In addition, the covers may include two layers as described above, or may include more than two layers, and the layers may be defined by laminated or multi-layer materials or not. In addition, the layers of the covers may be formed of any of numerous different materials, and may take any of numerous different shapes, that are currently known, or that later become known. Accordingly, this detailed description of the currently preferred embodiments of the present invention is to be taken in an illustrative sense, as opposed to a limiting sense.

What is claimed is:

1. A cover that is releasably attachable to a patient's skin having thereon a temporary tattoo or other marking identifying a set-up point for radiation therapy, the cover overlying the temporary tattoo or other marking and allowing the temporary tattoo or other marking to be visible therethrough, the cover comprising a flexible layer having a width or a diameter, shape, and thickness, and formed of a material, that, in combination, provide the flexible layer with characteristics that enable the flexible layer to be handled and adhesively attachable to the patient's skin over the temporary tattoo or other marking substantially without the flexible layer wrinkling during handling and attaching to the patient's skin for identifying a set-up point for radiation therapy, wherein the flexible layer comprises a lower surface and an opposing upper surface, the cover further comprising an adhesive covering substantially the entire lower surface and releasably engageable with the patient's skin in a position overlying the temporary tattoo or other marking, wherein the adhesive and the flexible layer are substantially transparent and allow viewing of the temporary tattoo or other marking therethrough, and the flexible layer comprises indicia in the form of crosshairs printed on the upper surface of the flexible layer and outside the adhesive layer, wherein inner ends of the crosshairs are spaced relative to each other and define a substantially transparent portion therebetween and are configured to enable viewing the temporary tattoo or other marking through the substantially transparent portion during placement of the cover over the temporary tattoo or other marking.

2. A cover as defined in claim 1, wherein a portion of the substantially transparent portion is located between the inner ends of the crosshairs and defines a viewing region between the inner ends of the crosshairs located at approximately a center of the cover.

3. A cover as defined in claim 1, wherein the inner ends of the crosshairs are radially spaced relative to each other on opposite sides of the substantially transparent portion.

4. A cover as defined in claim 1, wherein the indicia is substantially opaque.

5. A cover as defined in claim 1, wherein the indicia is a skin-contrasting color.

6. A cover as defined in claim 1, wherein the indicia is a dark color.

7. A cover as defined in claim 1, wherein a portion of the substantially transparent portion is located between the inner ends of the crosshairs and defines a diameter or width between the inner ends of the crosshairs that is within a range of about ⅛ inch to about 3/16 inch.

8. A cover as defined in claim 1, wherein a line thickness of the indicia is within a range of about 0.02 inch to about 0.1 inch.

9. A cover as defined in claim 1, wherein the flexible layer is configured to remain adhesively attached to the patient's skin to one or more of (a) preserve or prevent wear or removal of the temporary tattoo or other marking during an entire time period of a radiation treatment or therapy cycle of the patient, or (b) maintain the flexible layer over the temporary tattoo or other marking during an entire time period of a radiation treatment or therapy cycle of the patient.

10. A cover as defined in claim 1, wherein the adhesive does not contain an ink.

11. A method comprising releasably attaching a cover to a patient's skin having thereon a temporary tattoo or other marking identifying a set-up point for radiation therapy, for covering the temporary tattoo or other marking, and allowing the temporary tattoo or other marking to be visible therethrough, the cover comprising a flexible layer having a width or a diameter, shape, and thickness, and formed of a material, that, in combination, provide the flexible layer with characteristics that enable the flexible layer to be handled and adhesively attachable to the patient's skin over the temporary tattoo or other marking substantially without the flexible layer wrinkling during handling and attaching to the patient's skin for identifying a set up point for radiation therapy, wherein the flexible layer comprises a lower surface and an opposing upper surface, the cover further comprising an adhesive covering substantially the entire lower surface and releasably engageable with the patient's skin in a position overlying the temporary tattoo or other marking, wherein the adhesive and the flexible layer are substantially transparent and allow viewing of the temporary tattoo or other marking therethrough, and the flexible layer comprises indicia in the form of crosshairs printed on the upper surface of the flexible layer and outside the adhesive layer, wherein inner ends of the crosshairs are spaced relative to each other to define a substantially transparent portion therebetween and are configured to enable viewing the temporary tattoo or other marking through the substantially transparent portion during placement of the cover over the temporary tattoo or other marking;

the attaching step comprising:
(i) viewing the temporary tattoo or other marking for identifying a set-up point for radiation therapy through the substantially transparent portion;
(ii) substantially aligning the substantially transparent portion between the inner ends of the crosshairs with the temporary tattoo or other marking;
(iii) placing the adhesive-containing lower surface of the flexible layer of the cover onto the patient's skin and, in turn, adhesively attaching the flexible layer of the cover to the skin without substantially wrinkling the flexible layer and with the temporary tattoo or other marking visible through the substantially transparent portion between the inner ends of the crosshairs.

12. A method as defined in claim 11, wherein the attaching step includes attaching a cover wherein the indicia is at least one of substantially opaque and a skin-contrasting color.

13. A method as defined in claim 11, further comprising substantially aligning the indicia with the temporary tattoo or other marking to allow the temporary tattoo to be viewed through the substantially transparent portion.

14. A method as defined in claim 11, wherein the placing step includes manually placing the adhesive-coated surface onto the patient's skin and manually pressing the cover toward the skin.

15. An apparatus including a plurality of covers that are releasably attachable to a portion of a patient's skin having thereon a temporary tattoo or other marking identifying a set-up point for radiation therapy for covering the marking and allowing the temporary tattoo or other marking to be visible therethrough, the apparatus comprising:

a carrier substrate defining a releasable surface thereon;
the plurality of covers comprising relatively flexible layers spaced without touching each other on the releasable surface of the carrier substrate, each flexible layer being substantially transparent and having an upper surface, an opposing adhesive lower surface releasably superimposed on the releasable surface a width or a diameter, shape, and thickness, and formed of a material, that, in combination, provide said flexible layer with characteristics that enable said flexible layer to be 1) removable from the releasable surface without substantially wrinkling; and 2) attachable to the patient's skin with substantially the entire adhesive lower surface adhesively engaging the skin substantially without wrinkling and in a position with the lower and upper surfaces overlying the temporary tattoo or other marking and allowing the temporary tattoo or other marking to be visible through the substantially transparent flexible layer for identifying a set-up point for radiation therapy; and
indicia in the form of crosshairs printed on the upper surface of the flexible layer and outside of the adhesive lower surface, wherein inner ends of the crosshairs are spaced relative to each other and define a substantially transparent central portion therebetween and are configured to enable viewing the temporary tattoo or other marking through the substantially transparent central portion during placement of the cover over the temporary tattoo or other marking.

16. An apparatus as defined in claim 15, wherein the substantially transparent central portion, between the inner ends of the crosshairs, defines a viewing region between the inner ends of the crosshairs located at approximately a center of the cover.

17. An apparatus as defined in claim 15, wherein the inner ends are radially spaced relative to each other.

18. An apparatus as defined in claim 15, wherein the indicia is substantially opaque.

19. An apparatus as defined in claim 15, wherein the indicia is a skin-contrasting color.

20. An apparatus as defined in claim 15, wherein the indicia is a dark color.

21. An apparatus as defined in claim 15, wherein a diameter or width of the substantially transparent central portion, between the inner ends of the crosshairs, is within a range of about 1/8 inch to about 3/16 inch.

22. An apparatus as defined in claim 15, wherein a line thickness of the indicia is within a range of about 0.02 inch to about 0.1 inch.

23. An apparatus as defined in claim 15, wherein the lower adhesive surface is for remaining adhesively attached to the patient's skin to one or more of (a) preserve or prevent wear or removal of the temporary tattoo or other marking during an entire time period of a radiation treatment or therapy cycle of the patient, or (b) maintain the cover over the temporary tattoo or other marking during an entire time period of a radiation treatment or therapy cycle of the patient.

24. An apparatus including a plurality of covers that are releasably attachable to a portion of a person's skin having thereon a temporary tattoo or other marking identifying a set-up point for radiation therapy for covering the temporary tattoo or other marking and allowing the temporary tattoo or other marking to be visible therethrough, the apparatus comprising:

a continuous carrier strip defining an uninterrupted releasable surface thereon;

the plurality of first means axially spaced relative to, and without touching each other on the releasable surface of the carrier strip with the uninterrupted releasable surface of the carrier strip extending between adjacent first means, for releasing from the releasable surface without wrinkling, and for flexible and removable adhesive attachment on a lower side thereof to the person's skin in a position overlying the temporary tattoo or other marking substantially without wrinkling thereof and being substantially transparent for allowing the temporary tattoo or other marking to be visible therethrough for identifying a set-up point for radiation therapy; and wherein each first means includes second means printed on an upper side thereof outside the lower side for adhesive attachment for locating the temporary tattoo or other marking visible through the substantially transparent first means and including inner ends spaced relative to each other and configured to enable viewing the temporary tattoo or other marking through a substantially transparent portion between said inner ends during placement of the cover over the temporary tattoo or other marking.

25. An apparatus as defined in claim 24, wherein the first means is for remaining adhesively attached to the person's skin to one or more of (a) preserve or prevent wear or removal of the temporary tattoo or other marking during an entire time period of a radiation treatment or therapy cycle of the person, or (b) maintain the first means over the temporary tattoo or other marking during an entire time period of a radiation treatment or therapy cycle of the person.

* * * * *

UNITED STATES PATENT AND TRADEMARK OFFICE
CERTIFICATE OF CORRECTION

| | |
|---|---|
| PATENT NO. | : 11,278,740 B2 |
| APPLICATION NO. | : 12/264204 |
| DATED | : March 22, 2022 |
| INVENTOR(S) | : Traboulsi et al. |

It is certified that error appears in the above-identified patent and that said Letters Patent is hereby corrected as shown below:

On the Title Page

Item (73) Assignee:
Please delete "BERKLEY CORPORATION"
Please insert --BEEKLEY CORPORATION--.

Signed and Sealed this
Thirty-first Day of May, 2022

*Katherine Kelly Vidal*

Katherine Kelly Vidal
*Director of the United States Patent and Trademark Office*